United States Patent [19]

Giroux et al.

[11] 4,130,653

[45] Dec. 19, 1978

[54] METHOD OF TREATING HYPERTENSION

[75] Inventors: Eugene L. Giroux, Cincinnati, Ohio; Nellikunja J. Prakash; Paul J. Schechter, both of Strasbourg, France

[73] Assignee: Merrell Toraude et Compagnie, Strasbourg, France

[21] Appl. No.: 892,213

[22] Filed: Mar. 31, 1978

[51] Int. Cl.² ............................................. A61K 31/40
[52] U.S. Cl. ................................. 424/274; 424/275; 424/285; 424/317
[58] Field of Search ............... 424/274, 275, 285, 317

[56] References Cited

U.S. PATENT DOCUMENTS

| 3,452,039 | 6/1969 | Buchanan et al. | 260/308 |
| 3,941,818 | 3/1976 | Abdel-Monem | 260/429.9 |

OTHER PUBLICATIONS

Foye et al., Pharm. Sci. 61, 1209 (1972).
Haskel et al., J. Med. Chem. 13, (1970) 697.
Rauazzoni et al., C.A. 57 98339 (1962).
Campaigne et al., J. Org. Chem. 21, 32 (1956).
Halestrap. Biochem. J. 148(1)85 (1975).

*Primary Examiner*—Allen J. Robinson
*Attorney, Agent, or Firm*—L. Ruth Hattan; Eugene O. Retter; George W. Rauchfuss, Jr.

[57] ABSTRACT

This invention relates to a novel method for the treatment of hypertension which comprises administering a compound of the formula:

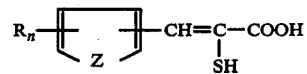

wherein Z is C=C, O, S, NH; R is hydrogen, methyl, ethyl, hydroxy, methoxy, ethoxy, chlorine, bromine, fluorine, iodine or trifluoromethyl; and n is 1, 2 or 3.

8 Claims, No Drawings

METHOD OF TREATING HYPERTENSION

BACKGROUND OF INVENTION

The use of the compounds employed in the present invention in the enhancement of serum and tissue zinc levels is described in copending U.S. application Ser. No. 765,420, filed Jan. 21, 1977. There is some evidence in the literature that zinc may have a protective role in certain cardiovascular related disorders and possibly in hypertension. (See, for example, Medical Clinics of North America 58, no. 2, 381 (1974)). Although it has been found that the α-mercapto-β-arylacrylic acids employed in the present invention enhance serum and tissue levels of zinc, the exact mechanism of action of the herein described α-mercapto-β-arylacrylic acids in the treatment of hypertension has not been delineated.

While α-mercapto-β-arylacrylic acids are well known, their utilization in therapeutics is exceedingly rare. We have made the unexpected discovery that the α-mercapto-β-arylacrylic acids described herein are useful in the treatment of hypertension. These compounds are most commonly prepared by the procedure of Campaigne, E. and Cline, R., J. Org. Chem. 21, 32 (1956) from rhodanine and the corresponding aryl aldehydes. U.S. Pat. No. 3,452,039 describes a number of α-mercapto-β-arylacrylic acids and their substitution products utilized as intermediates in the manufacture of benzothiophene hypocholesterolemic agents. Various α-mercapto-β-arylacrylic acids were prepared and tested by Ravazzoni, C., et al., Ann. Chim. (Rome) 52 305–12 (1962), Chem. Abst. 57, 9833g, and reported to be effective plant growth substances. Haskel, et al., J. Med. Chem. 13 697 (1970) prepared and tested α-mercapto-β-arylacrylic acids including substituted phenyl, substituted thienyl and substituted pyridyl analogs for neuraminidase inhibition and administered the most potent enzyme inhibitors, for example, α-mercapto-β-4-nitrophenyl acrylic acid orally and intraperitoneally to mice without increase in survival against influenza virus. Being interested in antibacterial and antifungal activity Foy, et al., J. Pharm. Sci. 61 1209 (1972) tested α-mercaptocinnamic acid as having some activity in this regard and incidentally relatively weak metal binding activity for copper, aluminum and iron. Activity in vitro in inhibiting rat heart mitochrondia pyruvate transport was reported for α-thio-2-furanopyruvate, otherwise named α-mercapto-β-2-furylacrylic acid by Halestrap, A., Biochem. J. 148 (1) 85 (1975) at page 90. No references more pertinent than these are known to applicants.

SUMMARY OF INVENTION

This invention relates to a method of treating hypertension in a patient in need thereof by administering to said patient α-mercapto-β-arylacrylic acid as defined by the following general Formula I or a pharmaceutically acceptable non-toxic salt thereof:

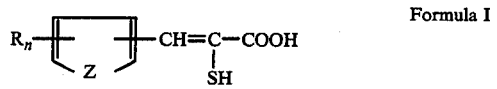

Formula I wherein Z is C=C, O, S, NH; R is H, CH$_3$, C$_2$H$_5$, OH, CH$_3$O, C$_2$H$_5$O, Cl, Br, F, I or CF$_3$; n is 1, 2 or 3.

DETAILED DESCRIPTION OF INVENTION

It is apparent from the foregoing general Formula I that the compounds employed in the present invention are α-mercapto-β-thienylacrylic acids, α-mercapto-β-furylacrylic acids, α-mercapto-β-pyrrylacrylic acids and α-mercapto-β-phenylacrylic acids and pharmaceutically acceptable non-toxic salts thereof wherein the aromatic ring, that is, the thienyl, furyl, pyrryl or phenyl ring may be further substituted with from 1 to 3 groups selected from methyl, ethyl, hydroxy, methoxy, ethoxy, chlorine, bromine, fluorine, iodine, or trifluoromethyl as illustrated respectively by the following Formulas II to V

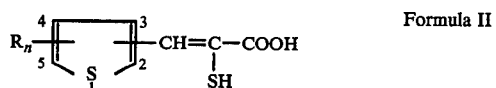

Formula II

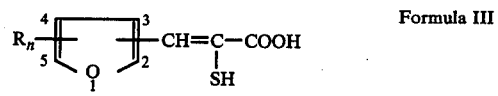

Formula III

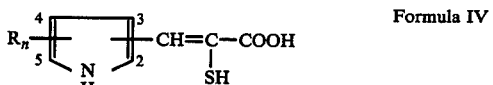

Formula IV

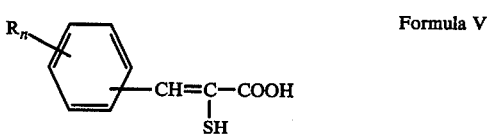

Formula V

In the above general Formulas II to V R and n have the meanings defined in Formula I.

In general Formulas II and III it is preferred that the α-mercapto-acrylic acid moiety, that is,

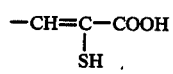

be attached to the 2-position of the furan or thiophene ring, and it is more preferred that within these groups of compounds when R is other than hydrogen that n be equal to 1 with the substituent as represented by R being attached at the 5-position of the furan or thiophene ring in the practice of the present invention. In general Formulas I to V, preferred substituent groups as represented by R are hydrogen, methyl, ethyl, hydroxy, chlorine, bromine and CF$_3$. Methoxy and ethoxy also represent preferred substituent groups as represented by R.

Illustrative species within the general Formula I are compounds wherein the aryl group is phenyl or substituted phenyl, for example, 2-, 3-, or 4-methyl, 2-, 3- or 4-ethyl, 2-, 3- or 4-bromo, 2-, 3- or 4-chloro, 2-, 3- or 4-fluoro, 2-iodo, 2,4-dichloro, 2,3-dichloro, 2,3,4-trichloro, 2-trifluoromethyl, 3-trifluoromethyl, 2-trifluoromethyl-3-chloro, 2-, 3- or 4-hydroxy, 2-, 3-or 4-methoxy, 2-, 3- or 4-ethoxy, 2-hydroxy-3-methoxy, 3-hydroxy-4-methoxy, 3-methoxy-4-hydroxy, 3-ethoxy-4-hydroxy, 2,3-dimethoxy, 2,4-dimethoxy, 2,5-dimethoxy, 2,6-dimethoxy, 3,4-dihydroxy, 3,4,5-trimethoxy, 2,3,4-trimethoxy, 3,5-dibromo-4-hydroxy; or other aryl groups in place of phenyl, namely, 2-furyl, 5-trifluoro-2-furyl, 5-methyl-2-furyl, 5-ethoxy- or 5-methoxy-2-furyl, 5-chloro-2-furyl; 3-furyl; 2-thienyl; or substituted thienyl, for example, 3-methyl, 5-methyl, 5-ethyl, 5-chloro, 5-bromo, 3-methoxy, 5-methoxy; 3-thienyl; 2-pyrryl; and 3-pyrryl; and pharmaceutically acceptable non-toxic salts thereof illustratively, sodium, potassium, calcium, aluminum, zinc, ammonium salts, amine salts, for example, trialkylamine, such as, triethylamine, dibenzylamine, glucosamine, of each of the above acids.

The most preferred embodiment of this invention is the use of compounds of general Formula I or a pharmaceutically acceptable salt thereof wherein R is hydrogen in the treatment of hypertension.

In practising the present invention the compounds of Formula I or a salt thereof either alone or in combination with acceptable pharmaceutical carriers are administered to the patient to be treated either orally or parenterally, for example, subcutaneously or intravenously. Compounds of general Formula I may be used in combination with one another. As used herein the term patient is taken to mean a warm blooded animal, such as, mammals, for example, humans having hypertension, or in other words, that are hypertensive. The term hypertension includes primary or essential hypertension, hormonally induced hypertension, renal hypertension and cadmium induced hypertension. A preferred mode of administration of the compounds of general Formulas I to V, in the practice of the present invention is oral administration.

The compounds of Formula I may be formulated for oral administration as solid or liquid unit dosage forms. The solid dosage forms can be tablets, coated or uncoated; capsules, hard or soft; powders; granules; pills, enteric coated if desired. Solid diluents and carriers may be lactose, starch or other innocuous material with the usual tableting adjuncts as desired. Liquid oral compositions may be dispersions, suspensions, elixirs, syrups or simple solutions in aqueous vehicle. Polyethylene glycols including polyethylene glycol 300 have been found convenient oral vehicles. The term unit dosage form as used in the specification and claims means physically discrete units suitable as unitary administration for humans, each unit containing a predetermined quantity of active ingredient to achieve the desired therapeutic effect in association with the pharmaceutical carrier. Sterile, intraperitoneal formulation with physiologically acceptable vehicle, for example, saline, optionally buffered can also be utilized.

The amount of compound administered will vary over a wide range depending upon the patient to be treated and the severity of the hypertension and will be any antihypertensive effective amount of from about 0.1 mg/kg to 20.0 mg/kg of body weight of the patient per day. For example, a unit dosage form may suitably contain about 250 mg of active ingredient as represented by Formula I or salt thereof.

The utility of the compounds of general Formula I in the treatment of hypertension has been demonstrated in chronic renal hypertensive rats, spontaneously hypertensive rats, in a DOCA-salt (deoxycorticosterone acetate) hypertensive model, and a cadmium induced hypertension model. The specific examples contained herein further demonstrate utility of the compounds employed in the present invention.

Preparation of the α-mercapto-β-arylacrylic acids of applicability herein is according to the method described by Campaigne, E. and Cline, P.E., J. Org. Chem. 21, 32 (1956) by condensing the corresponding carboxaldehyde II with rhodanine III and then splitting the products in alkaline medium, according to the general shceme:

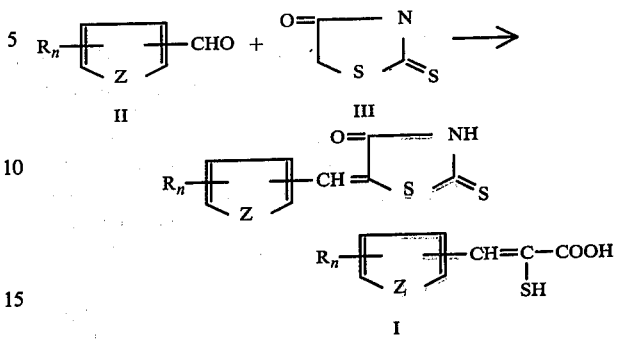

wherein Z, R and n are as defined in general Formula I. The corresponding carboxaldehydes and their preparation are well known in the art. The desired salts can of course by prepared by reaction between the hydroxide, carbonate or other basic metal, ammonium or amine compound and the free α-mercapto-β-arylacrylic acid in the usual manner.

While there has been some suggestion in the literature that the α-mercapto-β-arylacrylic acids are tautomeric with the thioketo acids, the concensus is that the compounds exist primarily in the mercapto acid form consistent with the chemical and physical properties, Campaigne and Cline, supra.

The following specific examples further illustrate the preparation and utilization of compounds employed in the instant invention.

EXAMPLE 1

α-Mercapto-β-(5-trifluoromethyl-2-furyl)acrylic acid

In a three necked flask, a mixture of 3.4 g of 5-trifluoromethyl-2-furfural, 2.92 g of rhodanine and 5.16 g of dry sodium acetate in 35 ml of glacial acetic acid is stirred and heated to reflux for two hours over a bath at 140°–145° C. After ten minutes a yellow precipitate forms. The reaction mixture is cooled, diluted with 30 ml of water, and the yellow precipitate is filtered, washed with water and dried. After chromatography over silica with dichloromethane as eluant, and recrystallization from dichloromethane and pentane, there is obtained 3.7 g (yield 63%) of yellow crystals of 5-(5-trifluoromethyl-2-furylmethylene)rhodanine. M.P. 174° C. $R_f = 0.41$ with 3% methanol/dichloromethane on silica gel

| Microanalysis | C | H | N | S |
|---|---|---|---|---|
| Calculated | 38.71 | 1.44 | 5.01 | 22.96 |
| Found | 38.70 | 1.56 | 5.10 | 22.91 |

NMR spectrum in $CDCl_3$ parts per million/tetramethyl silane 6.8 multiplet (ring protons) 7.38 singlet (exocyclic methylene)

1.58 g of the above 5-(5-trifluoromethyl-2-furylmethylene)rhodanine, 23 ml of 1 N sodium hydroxide solution and 25 ml of water are stirred under nitrogen at room temperature for 10 hours. After cooling with an ice bath and acidification with concentrated hydrochloric acid to pH 1.5, the resulting slurry is filtered to yield a slightly brown precipitate which is washed with 50 ml of water by stirring at room temperature under nitrogen and filtered to yield 0.8 g of slightly brown crystals (yield 60%) of α-mercapto-β-(5-trifluoromethyl-2-furyl)acrylic acid. M.P. 158° C.

| Microanalysis | C | H | S |
|---|---|---|---|
| Calculated | 40.34 | 2.11 | 13.46 |
| Found | 40.65 | 2.27 | 13.7 |

NMR in acetone (d 6) parts per million/tetramethylsilane 7.10 multiplet (ring protons) 7.6 singlet (exocyclic methylene)

EXAMPLE 2

α-Mercapto-β-Furanacrylic Acid, Renal Hypertension Model

In unanesthetized chronic renal hypertensive rats oral doses of 16, 40 and 100 mg/kg of α-mercapto-β-furanacrylic acid had no significant effect on systolic blood pressure and heart rate. Daily oral administration of α-mercapto-β-furanacrylic acid (40 mg/kg-day) slightly reduced systolic blood pressure of unanesthetized chronic renal hypertensive rats. In these experiments no significant effects on body weight or water intake were noted.

Devleopment of severe renal hypertension (clip 0.20mm) is inhibited from day 7 after the operation in rats treated once daily with 40 mg/kg (orally of α-mercapto-β-furanacrylic acid). Pronounced tachycardia observed in the hypertensive rats treated with vehicle was absent.

Table 1.

Effect of α-mercapto-β-furylacrylic acid (40 mg/kg; 10 ml/kg) on the development of renal hypertension in male rats. Unilateral renal artery clip 0.20 mm. Oral administration once daily in 25% PEG during 14 days. Means ± S.E.M. Administration was done at 9 A.M. Blood pressure and heart rate were measured 6–8 hours later.

|  | Systolic blood pressure (mm Hg) | | Heart rate (bpm) | |
|---|---|---|---|---|
|  | initial | after 14 days | initial | after 14 days |
| Vehicle (n=3) | 120 ± 2.1 | 214 ± 8.8 | 357 ± 8.9 | 492 ± 42.1 |
| α-mercapto-β- (n=7) furylacrylic acid | 123 ± 1.5 | 171 ± 9.9 | 371 ± 9.9 | 394 ± 26.3 |

EXAMPLE 3

α-Mercapto-β-furanacrylic acid, DOCA-salt hypertension

On the day that 2 DOCA pellets were implanted subcutaneously in rats, daily oral treatment with α-mercapto-β-furanacrylic acid was started. During the 15 day period of treatment the rise of systolic blood pressure was prevented. An initial decrease of blood pressure was observed. Total fluid intake (0.9% NaCl) of the treated rats amounted to 80–85% of that of the control. group. After 15 days the treatment was stopped and hypertension developed in both groups of rats during the next 6 weeks. A plateau of 170 mm Hg was reached. At day 56 the previous control rats were treated (period II). Blood pressure descreased to the normotensive control value. Despite continuation of the treatment blood pressure increased slowly during the next few days (Table 2). Heart rate was slightly lower during the control period and after 4 days of treatment in the group of rats receiving α-mercapto-β-furanacrylic acid. A small rise was observed in period II (Table 2).

Table 2.

Effect of RMI α-mercapto-β-furylacrylic acid (40 mg-kg; 10 ml/kg) on the development of DOCA-salt hypertension in male rats. Data in period I were obtained after 4 days of treatment (see Table 1 for details). Results of period II were obtained 6–8 hours after the first administration of α-mercapto-β-furylacrylic acid in this period. Data are means ± S.E.M. of 6–7 rats.

|  | Systolic blood pressure (mm Hg) | Heart Rate (bpm) |
|---|---|---|
|  | Control Period | |
| Vehicle | 124 ± 1.9 | 347 ± 7 |
| Test Compound | 123 ± 1.9 | 320 ± 8$^x$ |
|  | Period I | |
| Vehicle | 130 ± 1.4 | 385 ± 5 |
| Test Compound | 114 ± 1.8$^{xx}$ | 333 ± 10$^x$ |
|  | Period II | |
| Vehicle | 169 ± 2.6 | 305 ± 2 |
| Test Compound | 129 ± 8.6$^{xx}$ | 334 ± 13$^x$ |

$^x$p 0.05
$^{xx}$p 0.001

We claim:

1. A method of treating hypertension in a patient in need thereof which comprises administering to said patient an antihypertensive effective amount of an α-mercapto-β-arylacrylic acid of the formula:

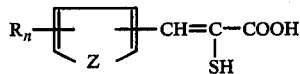

wherein Z is C=C, O, S or NH; R is H, CH$_3$, C$_2$H$_5$, OH, CH$_3$O, C$_2$H$_5$O, Cl, Br, F, I or CF$_3$; and n is 1, 2 or 3; or a pharmaceutically acceptable non-toxic salt thereof.

2. The method of claim 1 wherein R is H, CH$_3$, C$_2$H$_5$, OH, Cl, Br, 3. CF$_3$.

3. The method of claim 2 wherein Z is O or S and the aromatic ring is substituted at the 2,5-position.

4. The method of claim 1 wherein R is OCH$_3$ or OC$_2$H$_5$.

5. The method of claim 1 wherein the active ingredient is α-mercapto-β-phenyl-acrylic acid or a pharmaceutically acceptable non-toxic salt thereof.

6. The method of claim 1 wherein the active ingredient is α-mercapto-(2-furyl)-acrylic acid or a pharmaceutically acceptable non-toxic salt thereof.

7. The method of claim 1 wherein the active ingredient is α-mercapto-(2-thienyl)-acrylic acid or a pharmaceutically acceptable non-toxic salt thereof.

8. The method of claim 1 wherein the active ingredient is α-mercapto-(2-pyrryl)-acrylic acid or a pharmaceutically acceptable non-toxic salt thereof.

* * * * *